United States Patent
Toyoshima et al.

(10) Patent No.: US 7,267,860 B2
(45) Date of Patent: Sep. 11, 2007

(54) TOPSHEET OF ABSORBENT ARTICLE

(75) Inventors: Yasuo Toyoshima, Tochigi (JP); Ken Nemoto, Tochigi (JP); Wataru Saka, Tochigi (JP)

(73) Assignee: Kao Corporation, Tokyo (JP)

( * ) Notice: Subject to any disclaimer, the term of this patent is extended or adjusted under 35 U.S.C. 154(b) by 79 days.

(21) Appl. No.: 10/715,460

(22) Filed: Nov. 19, 2003

(65) Prior Publication Data
US 2004/0142151 A1    Jul. 22, 2004

(30) Foreign Application Priority Data
Nov. 19, 2002    (JP) ............... 2002-334527

(51) Int. Cl.
 B32B 3/00    (2006.01)
 B32B 5/14    (2006.01)
 A61F 13/20    (2006.01)

(52) U.S. Cl. .................. 428/156; 428/170; 428/171; 604/385.01

(58) Field of Classification Search .......... 428/156, 428/170, 172, 171; 604/385.01
See application file for complete search history.

(56) References Cited

U.S. PATENT DOCUMENTS

| | | | |
|---|---|---|---|
| 5,122,919 A | * | 6/1992 | Takemae et al. ............ 360/133 |
| 5,910,137 A | | 6/1999 | Clark et al. |
| 2002/0068150 A1 | | 6/2002 | Taneichi et al. |

FOREIGN PATENT DOCUMENTS

| | | |
|---|---|---|
| CH | 498234 | 5/1970 |
| CN | 1348026 A | 5/2002 |
| EP | 0423395 A1 | 4/1991 |
| EP | 1209271 A1 | 5/2002 |
| GB | 2031039 A | 4/1980 |
| JP | 2002-187228 A | 7/2002 |

* cited by examiner

*Primary Examiner*—Donald J. Loney
(74) *Attorney, Agent, or Firm*—Birch, Stewart, Kolasch & Birch, LLP

(57) ABSTRACT

A topsheet 10 of an absorbent article is a nonwoven fabric having a plurality of heat fusion joints 3 formed by embossing. Fibers constituting the nonwoven fabric protrude in the thickness direction of the nonwoven fabric between the joints 3 to form a plurality of protrusions 4a and 4b on both the upper and the lower sides of the nonwoven fabric. The base of the individual protrusions 4b formed on the lower side projects in the planar direction of the nonwoven fabric.

5 Claims, 2 Drawing Sheets

TOPSHEET OF ABSORBENT ARTICLE

This Nonprovisional application claims priority under 35 U.S.C. §119(a) on Patent Application No(s). 2002-334527 filed in JAPAN on Nov. 19, 2002, the entire contents of which are hereby incorporated by reference.

FIELD OF THE INVENTION

The present invention relates to a topsheet and other fibrous sheets used in absorbent articles such as sanitary napkins and disposable diapers. More particularly, it relates to a topsheet and fibrous sheets of an absorbent article which prevent wet-back of once absorbed liquid and easily conform to a wearer's movement.

BACKGROUND OF THE INVENTION

Assignee has proposed in JP-A-2002-187228 a bulky sheet exhibiting elastomeric behavior and breathability as a whole which contains a first layer and a second layer adjacent to the first layer, the first and the second layers being partially bonded together at joints in a prescribed pattern, the first layer having a three-dimensional shape between joints, and the second layer being made of a material exhibiting elastomeric behavior.

The bulky sheet referred to above shows sufficient recovery when extended in the planar direction and sufficient deformation when compressed in the thickness direction. Accordingly, this bulky sheet is fit for use as a topsheet of absorbent articles, such as sanitary napkins and disposable diapers. To cope with the requirements for these absorbent articles which are getting stricter, there still is a demand for a topsheet therefor with higher performance in terms of, e.g., resistance against wet-back of once absorbed liquid and conformability to a wearer's movement.

SUMMARY OF THE INVENTION

The present invention relates to a topsheet for an absorbent article which comprises a nonwoven fabric having a plurality of heat fusion joints formed by embossing, the fibers constituting the nonwoven fabric protruding in the thickness direction of the nonwoven fabric between the heat fusion joints to form a plurality of protrusions on both the upper and the lower sides of the nonwoven fabric, and the base of the individual protrusions formed on the lower side projecting in the planar direction of the nonwoven fabric The present invention also relates to a process of producing a fibrous sheet for the topsheet for an absorbent article which comprises a nonwoven fabric having a plurality of heat fusion joints formed by embossing, the fibers constituting the nonwoven fabric protruding in the thickness direction of the nonwoven fabric between the heat fusion joints to form a plurality of protrusions on both the upper and the lower sides of the nonwoven fabric, and the base of the individual protrusions on the lower side projecting in the planar direction of the nonwoven fabric, wherein the nonwoven fabric has an upper layer and a lower layer adjacent to the upper layer, the protrusions formed on the upper side of the nonwoven fabric are made of the upper layer, and the protrusions formed on the lower side of the nonwoven fabric are made of the lower layer, the lower layer contains 50% by weight or more of self-crimping fiber which has been crimped, and the upper layer contains thermally fusible fiber which has substantially no heat shrinkability or does not shrink at or below the self-crimping starting temperature of the self-crimping fiber, which process comprises:

superposing an upper layer-forming material containing the thermally fusible fiber which has substantially no heat shrinkability or does not shrink at or below the self-crimping starting temperature of the self-crimping fiber and a lower layer-forming material containing 50% by weight or more of the self-crimping fiber on each other, embossing the two materials from the lower layer-forming material side to form a plurality of heat fusion joints by which the two materials are partially joined into a nonwoven fabric and simultaneously to preliminarily crimp part of the self-crimping fiber of the lower layer-forming material that is present around the individual heat fusion joints, and thermally treating the nonwoven fabric at or above the self-crimping starting temperature of the self-crimping fiber to shrink the lower layer-forming material thereby to make the upper and the lower layer-forming materials protrude in the thickness direction of the nonwoven fabric to form a plurality of protrusions on both sides while making the base of the individual protrusions on the lower side of the nonwoven fabric project in the planar direction of the nonwoven fabric.

BRIEF DESCRIPTION OF THE DRAWINGS

While the specification concludes with claims particularly pointing out and distinctly claiming the subject matter which is regarded as forming the present invention, it is believed that the present invention will be better understood from the following description which is taken in conjuction with the accompanying drawings, in which like designations are used to designate substantilly identical elements, and in which:

DETAILED DESCRIPTION OF THE INVENTION

The present invention relates to a topsheet and other fibrous sheets of absorbent articles which prevent liquid wet-back and easily conform to a wearer's movement.

Figure 1:
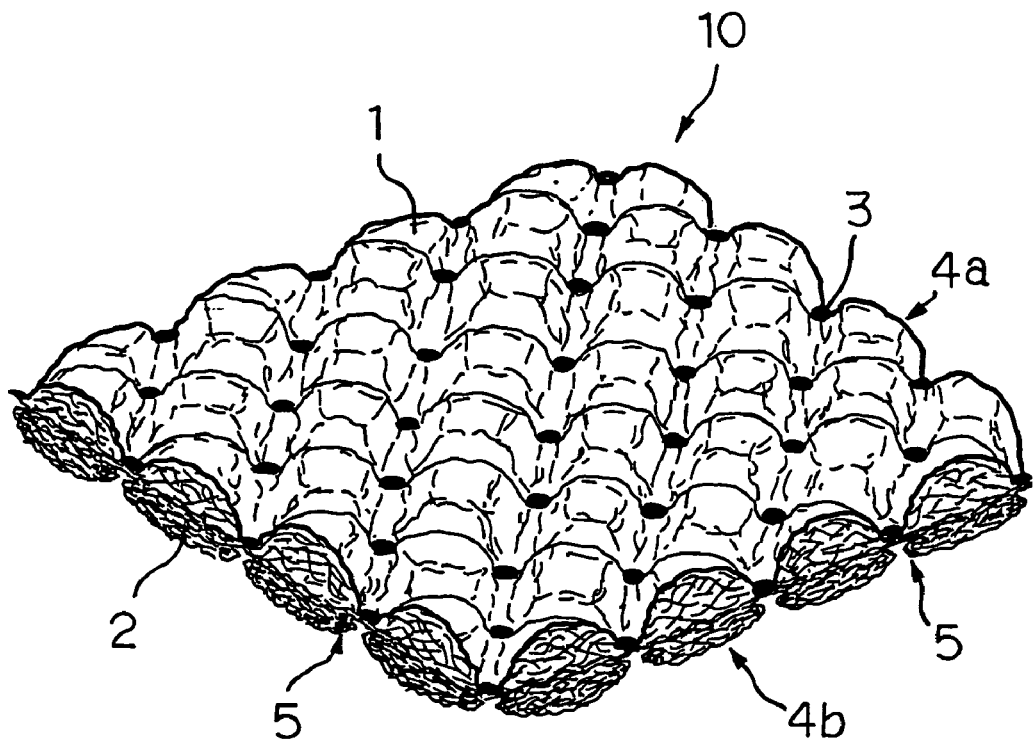
FIG. 1 is a perspective view of a topsheet according to an embodiment of the present invention.
Figure 2:
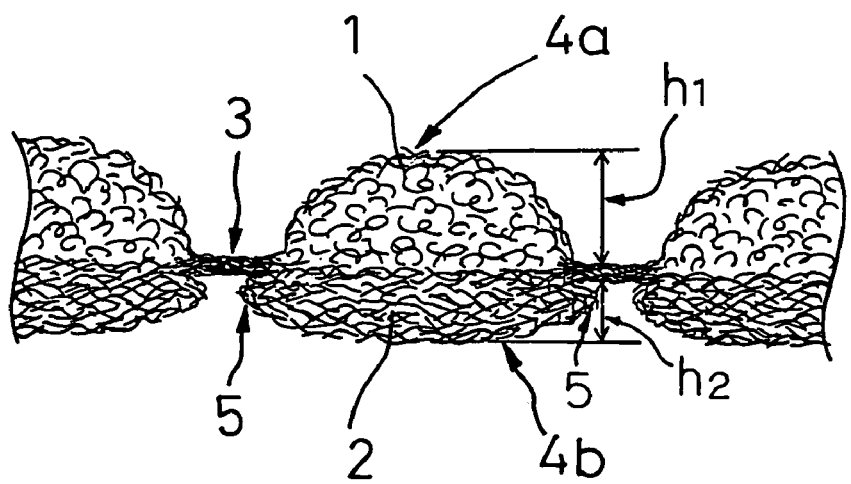
FIG. 2 is a cross-sectional view of the topsheet shown in FIG. 1.

The present invention will be explained based on the preferred embodiments with reference to the accompanying drawings. FIG. 1 is a perspective view of a topsheet of the absorbent article (referred to as simply a topsheet hereinafter) according to an embodiment of the present invention, and FIG. 2 is a cross-sectional view of the topsheet shown in FIG. 1.

The topsheet 10 shown in FIG. 1 is a double-layered nonwoven fabric having an upper fiber layer 1 and a lower fiber layer 2 adjacent thereto. The upper fiber layer 1 is made of a fiber aggregate. The lower fiber layer 2 is made of a fiber aggregate different from the upper fiber layer 1 in kind and/or composition of constituent fibers. The upper fiber layer 1 and the lower fiber layer 2 are partially joined by a plurality of heat fusion joints 3 formed by embossing. In other words, the upper fiber layer 1 and the lower fiber layer 2 are not entirely bonded together over their whole area. The term "upper" as in "upper (fiber) layer" or "upper side" of the topsheet 10 is intended to mean the side that is to face a wearer's body when fabricated into an absorbent article. Accordingly, the term "lower" as in "lower (fiber) layer" or "lower side" means the side that is to face an absorbent member of the absorbent article.

The heat fusion joints 3, each having a circular dot shape, are discretely arranged to form a diamond lattice pattern as a whole. The individual joints 3 are densified parts having a smaller thickness and a higher density than other parts of the topsheet 10. The upper fiber layer 1 and the lower fiber layer 2 are united in their thickness direction by the heat fusion joints 3. The individual joints 3 may have an arbitrary shape, such as a circular dot as adapted in this embodiment, an elliptic shape, a triangular shape, a rectangular shape or a combination thereof. The joints 3 may be continuously formed to make a line pattern, such as a pattern of straight lines or curved lines.

The total area ratio of the joints 3 to the area of the topsheet 10 (total area ratio of the joints 3 per unit area of the topsheet 10) is, while subject to variation according to the use of the topsheet 10, preferably 4 to 35%, more preferably 5 to 30%, in order to assure bonding between the two fiber layers 1 and 2 while allowing the constituent fibers to rise to form the protrusions with sufficient height for bulkiness. Where the topsheet 10 is produced in accordance with the process hereinafter described, the total area ratio of the joints 3 before heat shrinkage is preferably 2 to 15%, more preferably 5 is to 10%.

In the topsheet 10 made of nonwoven fabric, the constituent fibers protrude in the thickness direction of the nonwoven fabric between joints 3 to provide a great number of protrusions 4a on the upper side and many protrusions 4b on the lower side of the nonwoven fabric as well. The protrusions 4a formed on the upper side (hereinafter referred to as upper protrusions 4a) are mainly made of the upper fiber layer 1. The protrusions 4b formed on the lower side (hereinafter referred to as lower protrusions 4b) are mainly made of the lower fiber layer 2. The topsheet 10 according to the embodiment has a plurality of closed parts each surrounded by the joints 3 arranged in a diamond lattice shape, and the upper fiber layer 1 and the lower fiber layer 2 in each of these parts protrude upward and downward to form the upper protrusions 4a and the lower protrusions 4b, respectively, as depicted in FIG. 2. Accordingly, when seen from above, the topsheet 10 has the individual upper protrusions 4a and the individual lower protrusions 4b at the same positions. The upper and lower protrusions 4a and 4b each have a dome shape. Each dome is filled with fibers constituting the respective layers. The joints 3 are depressions relatively with respect to the upper and lower protrusions 4a and 4b. Thus, the topsheet 10 is bulky as a whole with a plurality of protrusions and depressions on both sides.

As illustrated in FIG. 2, with the plane containing the joints 3 taken as a reference plane, the height h1 of the upper protrusions 4a is larger than the height h2 of the lower protrusions 4b. Preferably, the height h1 of the upper protrusions 4a is about 0.3 to 5 mm, while the height h2 of the lower protrusions 4b is about 0.1 to 3 mm. With this configuration, the topsheet 10 provides an absorbent article that gives a wearer comfort and hardly causes wet-back of once absorbed liquid. The height of the protrusions 4a and 4b can be measured by observing a cut area of the topsheet 10 under a microscope.

As shown in FIG. 2, the lower protrusions 4b have their base (for example, the parts near the joints 3) extended or projected in the planar direction of the topsheet 10 to form an overhanging projection 5 (hereinafter referred to as an overhang 5). The overhang 5 is formed around the whole circumference of each lower protrusion 4b when seen from below. Accordingly, each lower protrusion 4b depicts a nearly inverted letter "Ω" in its cross-sectional view. The overhang 5 extends in the planar direction, sheltering part of the joints 3. Fibers in the overhang 5 are predominantly oriented in the thickness direction of the topsheet 10 along the outer contour of the lower protrusion 4b, which can be confirmed under microscopic observation.

Having the lower protrusions 4b, the topsheet 10, when disposed on an absorbent member and fabricated into an absorbent article, provides a certain space between the lower surface of the topsheet 10 and the upper surface of the absorbent member. Therefore, liquid once absorbed by the absorbent member hardly wets back. In particular, when the topsheet 10 is pressed under a wearer's body pressure while worn, the overhangs 5 of the lower protrusions 4b show resistance against compression to help the topsheet 10 keep its thickness, which ensures reduction of wet-back. Furthermore, since the overhangs 5 extend so as to shelter part of the densified and hard joints 3, they exhibit increased resistance to compression and thereby reducing wet-back to the topsheet 10. Additionally, the fibers in the overhangs 5 are orientated in the thickness direction of the nonwoven fabric mainly along the contour of the lower protrusions 5b, which assures increased resistance against compression to prevent wet-back.

Figure 3:
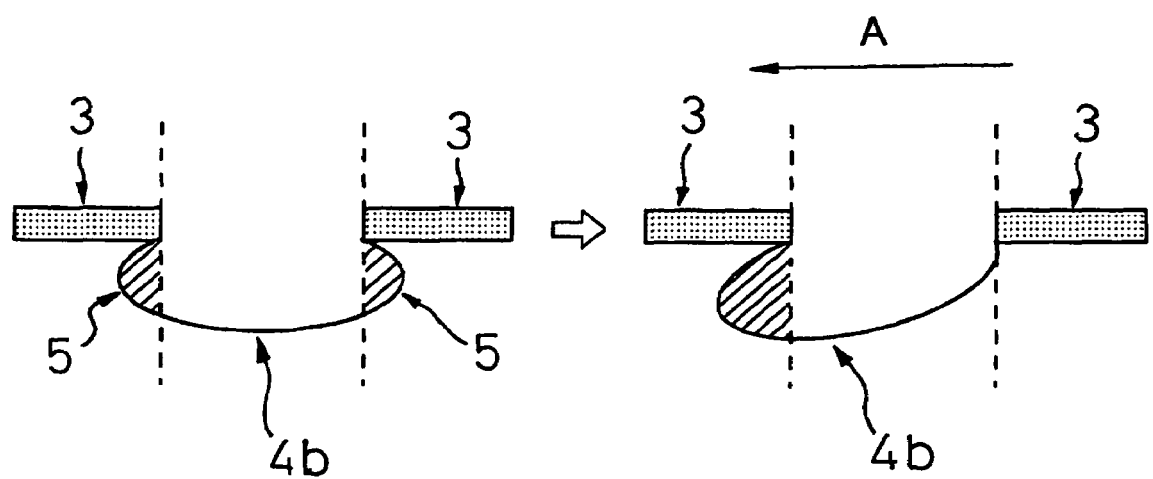
FIG. 3 is a schematic view illustrating movement in the horizontal direction of the topsheet of FIG. 1.

Besides the effect in reducing wet-back, the topsheet 10 of the present embodiment exhibits high conformability to a wearer's movement. As a result, an absorbent article having the topsheet 10 hardly shifts out of place while worn. In detail, since each lower protrusion 4b has the overhang 5 around its base to make an inverted letter "Ω" as previously stated, it has freedom of movement in the horizontal direction as illustrated in FIG. 3 (movement in the direction A). The lower protrusions 4b are therefore capable of moving independently of the upper protrusions 4a. When a wearer moves, the upper protrusions 4a are kept in place, while the lower protrusions 4b are capable of moving following the wearer's movement independently of the positions of the upper protrusions 4a. As a result, the absorbent article having the topsheet 10 is prevented from shifting out of place while being worn. Where the lower fiber layer 2 contains self-crimping fiber which has been crimped, namely, crimped fiber as described later, the lower fiber layer 2 exhibits extensibility and contractibility and thereby shows high recovery after stretch in the planar direction. This means that the topsheet 10 as a whole shows high recovery when stretched in the planar direction. Accordingly, the absorbent article having the topsheet 10 satisfactorily conforms to a wearer's movement with an improved fit and thereby prevents leakage effectively.

In addition to the above-mentioned effects, the topsheet 10 of the present embodiment is highly bulky because of the numerous protrusions 4a and 4b formed on both sides and shows excellent deformation to compression and recovery from compression. Where the lower fiber layer 2 contains crimped fiber as referred to above, the lower fiber layer 2 is extensible and contractible. Such an extensible and contractible lower fiber layer 2 extends and contracts freely following a wearer's movement while minimizing deformation of the upper fiber layer 1. Thus, the topsheet 10 has an extremely comfortable texture, and the absorbent article having the topsheet 10 gives a wearer comfortable feel.

The lower fiber layer 2 of the topsheet 10 according to the present embodiment contains self-crimping fiber in a helically crimped state. The self-crimping fiber suitably has a fineness of about 1 to 7 dtex. The self-crimping fiber includes conjugate fibers consisting of two thermoplastic polymers having different shrinkage percentages in an eccentric sheath/core configuration or a side-by-side configuration. Examples of such self-crimping conjugate fibers are given in JP-A-9-296325 and Japanese Patent 2759331. The two thermoplastic polymers having different shrinkage percentages include a combination of an ethylene-propylene random copolymer and polypropylene. A preferred content of the crimped fiber in the lower fiber layer 2 is 50% by weight or more, particularly 70 to 90% by weight, from the standpoint of formation of the upper protrusions 4a, the lower protrusions 4b, and the overhangs 5. The lower fiber layer 2 may be made solely of the crimped fiber. The other fiber which may constitute the lower fiber layer 2 in combination with the crimped fiber includes thermally fusible fiber which has substantially no heat shrinkability at or below the temperature causing the self-crimping fiber to start self-crimping (hereinafter referred to as a "self-crimping starting temperature"). Such fibers include thermally fusible fiber which has heat shrinkability but does not substantially shrink at the self-crimping starting temperature of the self-crimping fiber and thermally fusible fiber which has substantially no heat shrinkability. These thermally fusible fibers will hereinafter be inclusively referred to as "thermally fusible non-shrinking fiber".

In the lower protrusions 4b formed of the lower fiber layer 2, it is preferred that the crimped fibers be not fusion-bonded not only to each other but to other fibers present in the lower protrusions 4b so that the fibers in the lower protrusions 4b have high freedom to assure the freedom of the lower protrusions 4b in horizontal movement (see FIG. 3).

The upper fiber layer 1 contains thermally fusible non-shrinking fiber. Preferably, the upper fiber layer 1 is made up of thermally fusible conjugate fiber of sheath/core or side-by-side configuration. The upper fiber layer 1 may further contain the crimped fiber used in the lower fiber layer 2. Use of crimped fiber in the upper fiber layer 1 improves recovery of the upper protrusions 4a from compression and recovery of the topsheet 10 from planar extension. For obtaining these effects, a preferred content of the crimped fiber in the upper fiber layer 1 is 3 to 50% by weight, more preferably 10 to 30% by weight.

It is preferred for the lower fiber layer 2 to have been rendered hydrophilic to ensure smooth liquid passage. It is also preferred for the upper fiber layer 1 to have been rendered hydrophilic similarly. The lower fiber layer 2 desirably has higher hydrophilicity than the upper fiber layer 1 so as to prevent wet-back. Hydrophilization can be effected by, for example, applying a hydrophilizing agent to the fiber surface or incorporating a hydrophilizing agent into the fiber. In order to make the lower fiber layer 2 more hydrophilic than the upper fiber layer 1, water-absorbing fiber (e.g., cellulose fiber, cotton or rayon) may be mixed into the lower fiber layer 2.

The upper fiber layer 1 preferably has a basis weight of 10 to 100 g/m$^2$, more preferably 20 to 60 g/m$^2$. The lower fiber layer 2 preferably has a basis weight of 10 to 100 g/m$^2$, more preferably 20 to 60 g/m$^2$. Where the topsheet 10 is produced by the process described later, it is preferred to use an upper layer-forming material (an upper fiber layer before shrinkage) having a basis weight of 5 to 50 g/m$^2$, particularly 10 to 30 g/m$^2$. On the other hand, it is preferred to use a lower layer-forming material (a lower fiber layer before shrinkage) having a greater basis weight than the upper layer-forming material thereby to facilitate formation of the lower protrusions 4b. A preferred basis weight of the lower layer-forming material is 5 to 50 g/m$^2$, more preferably 10 to 30 g/m$^2$.

Having a relatively low fiber density in the upper protrusions 4a, the topsheet 10 exhibits sufficient deformability when compressed in the thickness direction. Preferably, the topsheet 10 has an apparent density of 0.005 to 0.05 g/cm$^3$, more preferably 0.01 to 0.05 g/cm$^3$, under a load of 0.5 cN/cm$^2$ so that it may feel bulky enough and exhibit compressive deformability to give a soft feel. It is also preferred for the topsheet 10 to have an apparent density of 0.04 to 0.1 g/cm$^3$, more preferably 0.05 to 0.08 g/mc$^3$, under a load of 50 cN/cm$^2$ so that it may have sufficient strength for retaining the three-dimensional contour of its protrusions. The load of 0.5 cN/cm$^2$ is almost equal to the pressure imposed to an absorbent article fitted to a wearer's body, and the load of 50 cN/cm$^2$ is almost equal to the wearer's body pressure imposed to an absorbent article.

The apparent density of the topsheet 10 under a load of 0.5 cN/cm$^2$ or 50 cN/cm$^2$ is calculated by dividing the basis weight by the thickness under the respective load as measured by the method described below.

From the standpoint of bulkiness and compressive deformability, a preferred thickness of the topsheet 10 is, while dependent on the intended use, 0.5 to 5 mm, more preferably 1 to 3 mm, at 0.5 cN/cm$^2$ and 0.2 to 3 mm, more preferably 0.5 to 2 mm, at 50 cN/cm$^2$.

The thickness under a load of 0.5 cN/cm$^2$ or 50 cN/cm$^2$ is measured with a compression tester KES-FB3 supplied by Kato Tech Co., Ltd. The KES-FB3 compression tester is designed to give a compression-recovery load to a specimen (e.g., fabric or film) by putting down and then lifting a 2 cm$^2$ disk indenter and to record a load-displacement hysteresis loop for a compression-recovery cycle, from which thickness, compression work, recovery and other data are obtained. A 2.5 cm-side square specimen cut out of a topsheet is set on the receiver of the tester. The indenter is moved down at a speed of 0.02 mm/sec to apply a compression load to the specimen. The distance between the indenter and the receiver, which corresponds to the thickness of the specimen, is measured when the compression load reaches 0.5 cN/cm$^2$ or 50 cN/cm$^2$.

The topsheet 10 preferably has a compressive deformation percentage of 30 to 85%, more preferably 40 to 70%, the compressive deformation percentage being calculated from the thickness at 0.5 cN/cm$^2$ (T1) and the thickness at 50 cN/cm$^2$ (T2) according to equation (1):

$$\text{Compressive deformation percentage (\%)} = (T1-T2)/T1 \times 100 \qquad (1)$$

The topsheet 10 having a compressive deformation percentage within the above range exhibits improved conformability to a wearer's body contour or movement and an improved texture when used as a member of an absorbent article.

In order to exhibit sufficient compressive deformability and bulkiness, the topsheet 10 preferably has a basis weight of 20 to 200 g/m$^2$, more preferably 40 to 150 g/m$^2$. The basis weight is determined by weighing a cut piece of the topsheet 10 having a size of 50 mm by 50 mm or larger by means of an electronic balance having a minimum readability of 1 mg and calculating the weight per square meter.

A preferred process for producing the topsheet 10 of the present embodiment will be described. An upper layer-forming material 1 and a lower layer-forming material 2 are prepared. The upper layer-forming material 1 includes a web or nonwoven fabric containing thermally fusible non-shrinking fiber. For example, thermally fusible non-shrinking fiber or, if desired, a mixture of thermally fusible non-shrinking fiber and self-crimping fiber is carded into a web, which can be used as an upper layer-forming material 1. The carded web may be made into an air-through nonwoven fabric by an air-through heat treatment, which is also useful as an upper layer-forming material 1. A web containing 50% by weight or more of self-crimping fiber is preferably used as a lower layer-forming material 2 so as to form lower protrusions 4b and overhangs 5. Use of a nonwoven fabric in place of a web can make it difficult to form lower protrusions 4b and overhangs 5.

The upper layer-forming material 1 and the lower layer-forming material 2 are superposed on each other and subjected to embossing to obtain a nonwoven fabric composed of the two materials partially joined at the heat fusion joints 3. Embossing can be carried out by means of a pair of rolls (i.e., an engraved roll and a smooth roll) heated to prescribed temperatures or an ultrasonic embossing machine. Whichever apparatus is used, the nonwoven fabric is embossed from the side of the lower layer-forming material 2 containing the self-crimping fiber. That is, where a pair of heated rolls are used, the lower layer-forming material 2 is brought into contact with the engraved roll, and the upper layer-forming material 1 with the smooth roll. Where an ultrasonic embossing machine is used, the lower layer-forming material 2 is brought into contact with an ultrasonic horn. By so doing, the self-crimping fibers of the lower layer-forming material 2 which are near the heat fusion joints 3 are preliminarily crimped and gathered around the joints 3. In order to effectively conduct preliminary crimping of the self-crimping fiber, the embossing temperature, i.e., the temperature of the embossing member of the apparatus in contact with the lower layer-forming material 2 should be sufficiently high. Preferably, the embossing temperature is higher than the self-crimping starting temperature of the self-crimping fiber by 5 to 30° C., preferably by 5 to 20° C. To preliminarily crimp the self-crimping fiber is important for helping the lower layer-forming material 2 form the lower protrusions 4b and the overhangs 5 on subsequent heat shrinkage and for controlling the fiber orientation in the overhangs 5.

On the other hand, the member of the embossing apparatus which comes into contact with the upper layer-forming material 1 does not need to have such high temperature. A temperature that assists formation of the heat fusion joints 3 would be sufficient. A recommended temperature of this member ranges from the melting point of the thermally fusible non-shrinking fiber contained in the upper layer-forming material 1 to a temperature higher than that melting point by about 10 to 20° C.

The resulting nonwoven fabric is then heat treated at or above the self-crimping starting temperature of the self-crimping fiber. The heat treatment is carried out by, for example, blowing hot air through the nonwoven fabric or irradiating the nonwoven fabric with infrared rays. By heat treatment, the lower layer-forming material 2 shrinks between the joints 3, whereas the upper layer-forming material 1 does not. As a result, the upper layer-forming material 1 protrudes in the thickness direction to form a plurality of upper protrusions 4a synchronously with the shrinkage of the lower layer-forming material 2. Non-shrinking of the upper layer-forming material 1 serves as resistance against shrinkage of the lower layer-forming material 2. That is, the lower layer-forming material 2 does not completely shrink in the planar direction but protrudes in the thickness direction to form lower protrusions 4b. Where the basis weight of the lower layer-forming material 2 falls within the above-recited range, formation of the lower protrusions 4b would be easier.

As stated previously, when the upper layer-forming material 1 and the lower layer-forming material 2 are partially bonded by embossing from the side of the lower layer-forming material 2, the self-crimping fibers near the joints 3 preliminarily self-crimp and gather around the joints 3. When the lower layer-forming material 2 shrinks and protrudes in this state, the preliminarily crimped fibers gathering around the joints 3 are further crimped and, at the same time, shifted along the contour of the protrusion while being oriented in the thickness direction of the nonwoven fabric. It follows that the base of each lower protrusion 4b projects in the planar direction of the nonwoven fabric to form an overhang 5.

In order to control the degree of shrinkage of the lower layer-forming material 2 to successfully form the lower protrusions 4b and the overhangs 5, the nonwoven fabric may be held by restraining means, such as a pin tenter, during the heat treatment. In this case, because the lower layer-forming material 2 shrinks almost isotropically in its planar direction, it is preferable that the whole periphery of the nonwoven fabric be held by the restraining means. The degree of shrinkage of the nonwoven fabric is preferably 30 to 80%, more preferably 30 to 60%, in terms of area shrinkage percentage. The area shrinkage percentage is represented by equation (2):

$$\text{Area shrinkage percentage (\%)} = (S_0 - S_1)/S_0 \times 100 \qquad (2)$$

where $S_0$ is the original area before shrinkage; and $S_1$ is the area after shrinkage.

An absorbent article having the thus prepared topsheet 10 hardly wets back and gives a wearer a dry and comfortable feel. Highly conformable to a wearer's movement, the absorbent article hardly shifts out of place and therefore prevents leakage.

The present invention is not limited to the above-described embodiment. While the topsheet of the embodiment is made of a double-layered nonwoven fabric, the topsheet of the invention can be made of a nonwoven fabric having a single layer structure or a multilayer structure composed of three or more layers. In making the topsheet of a single-layered nonwoven fabric, a web comprising self-crimping fiber and thermally fusible non-shrinking fiber is embossed to form heat fusion joints and then heat-treated to crimp the self-crimping fiber. In this case, the embossing temperature on one side of the web is set higher than that on the other side.

The topsheet 10 described above can be used as a fibrous sheet other than a topsheet in an absorbent article. For instance, it is useful as an intermediate fibrous sheet, so called "intermediate sheet" or "sub-layer sheet", disposed between a topsheet and an absorbent member. In this application, the fibrous sheet of the present invention is used with its upper fiber layer 1 facing the topsheet side, and the lower fiber layer 2 facing the absorbent member. The resulting absorbent article exhibits satisfactory absorptivity and reduced wet-back.

The present invention will now be illustrated in greater detail with reference to Examples. The following Examples are presented as being exemplary of the present invention and should not be considered as limiting.

EXAMPLE 1

(1) Preparation of Upper Fiber Layer

Sheath/core conjugate fiber NBF-SH (available from Daiwabo Co., Ltd.; core: polyethylene terephthalate; sheath: polyethylene; core/sheath weight ratio: 5/5; fineness: 2.2 dtex; fiber length: 51 mm) was carded into a web, which was heat-treated at 120° C. in an air-through system to prepare an air-through nonwoven fabric having a basis weight of 20 g/m², which was used as an upper layer-forming material.

(2) Preparation of Lower Fiber Layer

Self-crimping fiber (available from Daiwabo Co., Ltd.; thermally shrinkable sheath/core conjugate fiber having an ethylene-propylene random copolymer core and a polypropylene sheath; fineness: 2.2 dtex; self-crimping starting temperature: 90° C.) was carded into a web having a basis weight of 20 g/m², which was used as a lower layer-forming material.

(3) Preparation of Topsheet

The upper layer-forming nonwoven fabric and the lower layer-forming web prepared in (1) and (2) above were superposed on each other and passed through a heat embossing machine composed of an engraved roll and a smooth roll to join them with the lower layer-forming web in contact with the engraved roll so that embossing was conducted from the side of the lower layer-forming web. The engraved roll and the smooth roll were set at 175° C. and 125° C., respectively. The engraved roll had projections each having a circular shape with an emboss area of 0.047 cm² arrayed at a pitch of 7 mm in both the MD and the TD and a pitch of 5 mm in the direction forming 45° with the MD and the CD to make a diamond lattice pattern as a whole. The total emboss area ratio of the resulting nonwoven fabric was 7.2%.

The four sides of the resulting nonwoven fabric were fixed on the pins of a pin tenter adjusted to the size to which the nonwoven fabric was to shrink so that the nonwoven fabric might not overshrink than designed. The nonwoven fabric as caught on the pin tenter was heat treated in a hot air dryer set at 130° C. for 1 to 3 minutes to obtain a topsheet having a basis weight of 80 g/m². The area shrinkage percentage by this heat treatment is shown in Table 1. The resulting topsheet had protrusions on both the upper fiber layer side and the lower fiber layer side and overhangs at the base of each lower protrusion as shown in FIG. 2. On observing under an electron microscope, it was confirmed that the fibers constituting the lower protrusions were not fusion bonded and that the fibers in the overhangs were oriented predominantly in the thickness direction of the sheet along the contour of the lower protrusions.

EXAMPLE 2

Thermally fusible non-shrinking fiber and self-crimping fiber were mixed at a weight ratio of 85:15. The mixed fiber was carded into a web. The web was heat treated at 120° C. in an air-through system to obtain an air-through nonwoven fabric having a basis weight of 20 g/m². A topsheet having the structure shown in FIG. 2 was prepared in the same manner as in Example 1, except for using the above-prepared nonwoven fabric as an upper layer-forming material. The resulting topsheet had a basis weight of 80 g/m². On observing under an electron microscope, it was confirmed that the fibers constituting the lower protrusions were not fusion bonded and that the fibers in the overhangs were oriented predominantly in the thickness direction of the sheet along the contour of the lower protrusions.

EXAMPLE 3

A topsheet having the structure shown in FIG. 2 was prepared in the same manner as in Example 1, except for changing the basis weight of the upper layer-forming material to 15 g/m² and that of the lower layer-forming material to 35 g/m². The resulting topsheet had a basis weight of 100 g/m². On observing under an electron microscope, it was confirmed that the fibers constituting the lower protrusions were not fusion bonded and that the fibers in the overhangs were oriented predominantly in the thickness direction of the sheet along the contour of the lower protrusions.

EXAMPLE 4

A topsheet having the structure shown in FIG. 2 was prepared in the same manner as in Example 1, except for changing the basis weight of the upper layer-forming material to 16 g/m² and that of the lower layer-forming material to 16 g/m². The resulting topsheet had a basis weight of 65 g/m². On observing under an electron microscope, it was confirmed that the fibers constituting the lower protrusions were not fusion bonded and that the fibers in the overhangs were oriented predominantly in the thickness direction of the sheet along the contour of the lower protrusions.

COMPARATIVE EXAMPLE 1

A carded web prepared from self-crimping fiber was passed through a heat embossing machine composed of an engraved roll (set at 145° C.) and a smooth roll to obtain a heat-embossed nonwoven fabric having a basis weight of 20 g/m². The engraved roll had projections each having a circular dot shape with an emboss area of 0.0055 cm² regularly arrayed at an interval of 1.4 mm in both the MD and the TD. The total emboss area ratio of the resulting nonwoven fabric was 28%. A topsheet was prepared in the same manner as in Example 3, except for using the above-prepared heat-embossed nonwoven fabric as a lower layer-forming material. The resulting topsheet had a basis weight of 60 g/m². The topsheet had neither lower protrusions nor overhangs.

COMPARATIVE EXAMPLE 2

The topsheet of a commercially available sanitary napkin, Laurier® Sarasara Cushion Slim with no wings (Laurier UN-f) available from Kao Corp. was removed and evaluated. The topsheet was a nonwoven fabric produced by carding sheath/core conjugate fiber NBF-SH (available from Daiwabo Co., Ltd.; core: polyethylene terephthalate; sheath: polyethylene; core/sheath weight ratio: 5/5; fineness: 2.2 dtex; fiber length: 51 mm) into a web and heat-embossing the web. The basis weight of the nonwoven fabric was 25 g/m². The nonwoven fabric had perforations.

COMPARATIVE EXAMPLE 3

The topsheet of a commercially available sanitary napkin Whisper™ (Whisper Wga1-a) available from The Procter & Gamble Company was removed and evaluated. The topsheet was a perforated polyethylene film to which heat-embossed nonwoven fabric was fixed.

Evaluation:

The topsheets prepared in Examples and Comparative Examples were microscopically observed to measure the thickness of the upper protrusions ($h1$) and of the lower protrusions ($h2$). The apparent density and thickness of the topsheets were measured under loads of 0.5 cN/cm² and 50 cN/cm² in accordance with the method described supra. Furthermore, the topsheets were evaluated in terms of thickness deformation under unit load (gf/cm$^2$), wet-back under pressure, and liquid spread area in accordance with the methods described infra. The results obtained are shown in Table 1.

(a) Thickness Deformation

A 2.5 cm-side square specimen cut out of a topsheet was set in a compression tester KES-FB3 supplied by Kato Tech Co., Ltd. (the mechanism of measurement has been described). The indenter was moved down at a speed of 0.02 mm/sec to apply a compression load to the specimen until the load reached 50 gf/cm$^2$. The thicknesses of the specimen at 10 gf/cm$^2$ (t1) and at 0.5 gf/cm$^2$ (t2) were measured. The difference between t2 and t1 (mm) was divided by 10 to obtain a thickness deformation per gf/cm$^2$. The thickness deformation thus calculated is a measure of compressibility under a relatively low pressure of 10 gf/cm$^2$, i.e., softness of the topsheet.

(b) Wet-Back Under Pressure

The absorbent member was taken out of Laurier UN-f described supra. Three grams of defibrinated horse blood (available from Nippon Biotest Lab.) was poured into the isolated absorbent member. An 80 mm wide and 100 mm long topsheet was superposed on the upper side of the absorbent member with its lower fiber layer facing down. An acrylic resin plate large enough to cover the entire area of the topsheet was put thereon to give a load of 50 g/cm$^2$. Three minutes later, the resin plate was removed, and any blood adhered to the plate was completely wiped off with filter paper (available from Toyo Roshi Kaisha, Ltd.) whose weight had previously been measured. The filter paper having absorbed blood was weighed again. The weight gain of the filter paper was taken as wet-back.

(c) Liquid Spread Area

The topsheet of a commercially available sanitary napkin Laurier UN-f was stripped and replaced with a 70 mm wide and 100 mm long topsheet to be tested. The resulting sanitary napkin was stuck to the crotch portion of a sanitary garment (Laurier® Standard shorts, available from Kao Corp.). The sanitary garment with the sanitary napkin was put on a movable female body model. After the model was operated to take a walking movement for 1 minute, 3 g of defibrinated horse blood was poured into the napkin at a rate of 2 g/15 sec, and the model was operated to take the same walking movement for an additional 30 minute period. The napkin was removed, and the blood spread area on the topsheet was measured with an image analyzer. The spread area is a measure for positional shift of the napkin due to a wearer's movement.

TABLE 1

|  |  | Example | | | | Comparative Example | | |
| --- | --- | --- | --- | --- | --- | --- | --- | --- |
|  |  | 1 | 2 | 3 | 4 | 1 | 2 | 3 |
| Basis | Upper layer-forming material | 20 | 20 | 15 | 16 | 15 | — | — |
| weight | Lower layer-forming material | 20 | 20 | 35 | 16 | 20 | — | — |
| (g/m$^2$) | Topsheet (after shrinkage) | 80 | 80 | 100 | 65 | 60 | 25* | 25* |
|  | Upper protrusion height h1 (mm) | 1.7 | 1.7 | 1.8 | 1.6 | 1.9 | 0.42 | 0.50 |
|  | Lower protrusion height h2 (mm) | 0.9 | 0.9 | 1.2 | 0.8 | 0.45 | — | — |
|  | Topsheet thickness at 0.5 cN/cm$^2$ (mm) | 2.6 | 2.6 | 3 | 2.4 | 2.4 | 0.42 | 0.5 |
|  | Density at 0.5 cN/cm$^2$ (g/cm$^3$) | 0.031 | 0.031 | 0.033 | 0.027 | 0.027 | — | — |
|  | Topsheet thickness at 50 cN/cm$^2$ (mm) | 1.4 | 1.4 | 1.3 | 1.2 | 0.5 | — | — |
|  | Density at 50 cN/cm$^2$ (g/cm$^3$) | 0.057 | 0.057 | 0.077 | 0.052 | 0.13 | — | — |
|  | Area shrinkage percentage (%) | 46 | 46 | 57 | 50 | 79 | — | — |
|  | Thickness deformation [mm/(gf/cm$^2$)] | 0.08 | 0.07 | 0.08 | 0.08 | 0.08 | 0.05 | 0.01 |
|  | Wet-back (mg) | 0.5 | 0.5 | 0.5 | 0.8 | 2.5 | 5.0 | 2.0 |
|  | Liquid spread area (cm$^2$) | 6 | 6 | 7 | 7 | 13 | 23 | 17 |

*Not shrunken

As is clearly seen from the results in Table 1, all the topsheets of the Examples are soft and have reduced wet-back. It is also seen that these topsheets suppress the spread of absorbed liquid, which proves that the lower fiber layer follows the movement of a wearer.

As described above, the topsheet's other fibrous sheets of the present invention for use in absorbent articles prevents wet-back and is capable of following a wearer's movement. Therefore, an absorbent article having these sheets of the present invention gives a wearer a dry and comfortable feel with reduced wet-back and is kept in place while worn to cause little leakage.

The invention having been thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application No. 2002-334527 filed Nov. 19, 2002, which is incorporated herein by reference.

What is claimed is:

1. A fibrous sheet for an absorbent article which comprises a nonwoven fabric having a plurality of heat fusion joints formed by embossing fibers constituting the nonwoven fabric protruding in the thickness direction of the nonwoven fabric between the heat fusion joints to form a plurality of protrusions on both the upper and the lower sides of the nonwoven fabric, and the base of the individual protrusions formed on the lower side projecting laterally in the planar direction of the nonwoven fabric and extending at least partially over an adjacent heat fusion joint.

2. The fibrous sheet according to claim 1, wherein the nonwoven fabric has an upper layer and a lower layer adjacent to the upper layer, the protrusions formed on the upper side of the nonwoven fabric are made of the upper layer, and the protrusions formed on the lower side of the nonwoven fabric are made of the lower layer, the lower layer contains 50% by weight or more of self-crimping fiber which has been crimped, and the upper layer contains thermally fusible fiber which has substantially no heat shrinkability or does not shrink at or below the self-crimping staffing temperature of the self-crimping fiber.

3. The fibrous sheet according to claim 2, wherein in the protrusions made of the lower layer, the self-crimping fibers which has been crimped are free from each other without being fusion bonded.

4. The fibrous sheet according to claim 1, wherein the height of the protrusions formed on the upper side of the nonwoven fabric is larger than that of the protrusions formed on the lower side of the nonwoven fabric.

5. The fibrous sheet according to claim 1, which comprises a topsheet for said absorbent article.

* * * * *